(12) United States Patent
Robertson et al.

(10) Patent No.: US 6,833,111 B2
(45) Date of Patent: Dec. 21, 2004

(54) MULTIPLE ANALYTE ASSAYING DEVICE WITH A MULTIPLE SAMPLE INTRODUCTION SYSTEM

(75) Inventors: John L. Robertson, Fisher, IN (US); Jane Tsai, Indianapolis, IN (US); Lawrence C. McPhee, Irvine, CA (US); Steven S. Bachand, Laguna Niguel, CA (US); Robert L. Grenz, Santa Ana, CA (US); Dennis D. Blevins, Laguna Hills, CA (US)

(73) Assignees: Varian, Inc., Palo Alto, CA (US); Roche Diagnostics Corp., Indianapolis, IN (US)

( * ) Notice: Subject to any disclaimer, the term of this patent is extended or adjusted under 35 U.S.C. 154(b) by 139 days.

(21) Appl. No.: 09/834,769

(22) Filed: Apr. 13, 2001

(65) Prior Publication Data

US 2002/0150501 A1 Oct. 17, 2002

(51) Int. Cl.[7] .............................................. G01N 33/48
(52) U.S. Cl. ........................ 422/58; 422/61; 436/164; 436/169; 436/808; 600/584
(58) Field of Search .............................. 422/56, 58, 61; 436/164, 166, 169, 174, 176, 808–810, 901; 600/572–573, 583, 584

(56) References Cited

U.S. PATENT DOCUMENTS

| | | | |
|---|---|---|---|
| 4,696,797 A | 9/1987 | Kelton | 422/101 |
| 4,900,863 A | 2/1990 | Schmidt et al. | 560/41 |
| 5,028,535 A | 7/1991 | Buechler et al. | 435/7.1 |
| 5,089,391 A | 2/1992 | Buechler et al. | 435/7.1 |
| 5,202,268 A | 4/1993 | Kuhn et al. | 436/525 |
| 5,468,648 A | 11/1995 | Chandler | 436/518 |
| 5,559,041 A | 9/1996 | Kang et al. | 436/518 |
| 5,602,040 A | 2/1997 | May et al. | 436/514 |
| 5,622,871 A | 4/1997 | May et al. | 436/514 |
| 5,656,448 A | 8/1997 | Kang et al. | 435/7.94 |
| 5,656,503 A | 8/1997 | May et al. | 436/514 |
| 5,658,801 A | 8/1997 | Poissant et al. | |
| 5,798,273 A | 8/1998 | Shuler et al. | 436/514 |
| D404,812 S | 1/1999 | Cipkowski | D24/107 |
| 5,948,695 A * | 9/1999 | Douglas et al. | 436/518 |
| 5,976,895 A | 11/1999 | Cipkowski | 436/518 |
| D420,141 S | 2/2000 | Casterlin | D24/223 |
| 6,027,943 A | 2/2000 | Kang et al. | 436/518 |
| D423,110 S | 4/2000 | Cipkowski | D24/225 |
| 6,087,185 A | 7/2000 | Lee-Own et al. | 436/514 |
| 6,203,757 B1 * | 3/2001 | Lu et al. | 422/58 |

FOREIGN PATENT DOCUMENTS

| | | |
|---|---|---|
| WO | WO 00/20862 A1 | 4/2000 |
| WO | WO 00/37939 | 6/2000 |

* cited by examiner

*Primary Examiner*—Lyle A. Alexander
(74) *Attorney, Agent, or Firm*—Walter A. Hackler

(57) ABSTRACT

A multiple analyte assaying device includes a casing having a pocket portion adapted to capture or contain a predetermined volume of fluid specimen to be assayed. Disposed within the casing is a sample receiving pad and one or more reagent test strips. The pocket portion of the casing includes a feed element having multiple feed inlets, or alternatively, a single feed slot. The feed element provides pressure against the sample receiving pad. The pressure against the pad and a small size of the inlet or inlets are effective in controlling a rate of fluid release of the specimen to the sample receiving pad. The casing includes observation windows or alternatively a clear plastic view area for enabling observation of reagent zones of the test strips. The device is structured and adapted to enable a technician to capture the appropriate volume of fluid specimen in the pocket portion by submerging or dipping a portion of the device into a fluid-filled collection container for a brief period of time. The device includes a rail depending from the casing for elevating the dampened portion of the casing when the device is placed on a level surface.

5 Claims, 4 Drawing Sheets

MULTIPLE ANALYTE ASSAYING DEVICE WITH A MULTIPLE SAMPLE INTRODUCTION SYSTEM

The present invention generally relates to an assaying device and more specifically relates to an analyte assaying device with a multiple sample introduction system.

Devices for testing for the presence of single or multiple substances, (i.e. "analytes") in a single fluid sample, for example a urine or blood specimen, are well known. The demand for inexpensive, accurate and simple to use devices for testing, or assaying, biological specimens has increased in recent years. Various commercial assaying devices are available for use in hospitals, clinics, research laboratories, at home and in the workplace. Following now are some specific, common examples illustrating the use of assaying devices. For example, in a hospital setting, patients are often subjected to massive dosages of antibiotics to defeat an infection, and thereafter a small amount of blood may be withdrawn from the patient and the serum assayed for determining if an appropriate amount of antibiotic is present in the blood. As another specific example, in a hospital emergency room where an overdose patient has impaired cognitive function, or is a small child unable to communicate, the type of drug overdosed may be quickly determined using an available assaying device in order to ensure correct administration of treatment. Assaying devices are commonly used in other settings as well. For example, many employers now routinely administer so called "drug tests" to prospective and current employees in order to maintain a safe work environment. In addition, pregnancy and fertility test kits adapted for "in home" use, are now widely available to consumers. Such test kits include assaying devices which are, for the most part, accurate, and very easy to use.

A common form of assaying device is a lateral flow test device which generally includes a porous element of nitrocellulose or paper, typically in strip form, having chemical reagents striped or incorporated onto specific regions, or "zones" thereof. One zone may include a specific binding reagent for the analyte, bearing a visible label such as a colored latex particle. The labeled reagent is incorporated onto the porous element in a manner that allows it to freely migrate through the porous material, in the presence of a liquid specimen sample. Another zone, spatially distinct from the first zone, may include an unlabeled specific binding reagent having specificity for same analyte as the first zone, and which is capable of participating with the labeled reagent in either a "sandwich" or "competition" reaction. The unlabeled specific binding reagent may be firmly immobilized on the porous element such that it is not free to migrate through the porous material, even in the moist state. In a "sandwich" type assay, any analyte present in the specimen sample will become labeled as it is carried through the porous element and bound, where its presence is manifested by a detectable color change.

Many such test devices for detecting body fluid components are capable of making not only qualitative, but also quantitative or semi-quantitative measurements. Thus, by observing a color change response after a certain period of time, an analyst can obtain not only a positive indication of the presence of a specific component, but also an estimate of how much of the component is present in the sample.

Assaying devices may take the form of a dip-and-read type device, in which one portion of the porous element is immersed in a specimen sample, such as in a collection cup, or a urine stream. May et al. U.S. Pat. No. 5,602,040 issued on Feb. 11, 1997, discloses such a dip-and-read type device which includes an elongated case having a porous test strip disposed within, and a protective, removable cap or shroud. The cap is used to cover a sample receiving member protruding from the casing, after the sample receiving member has been contacted with a urine specimen. Other assaying devices are designed to be placed horizontally on a table top and include a case enclosing a porous test element, the casing typically including a receptacle in which a measured amount of specimen sample is deposited using a syringe, for example.

Conventional assaying devices have also been developed which include multiple lateral flow test elements which allow for detection of more than one type of analyte in a single fluid specimen. For example, U.S. Pat. No. 5,976,895 issued to Cipkowski on Nov. 2, 1999 discloses such a device. The Cipkowski device includes a transparent container having a lid with a slit for receiving a single test card having multiple test strips. Procedure of use requires a test subject to fill the container with a urine specimen, and place the lid on the container. The test card with multiple strips is then manually inserted through the slit in the lid such that a portion of each strip is immersed in the specimen. Each strip absorbs some of the specimen. The card is left in the container for a period of time and test results are read on the test card by observation through the transparent container walls.

Although these and other assaying devices are generally easy to use in both a clinical and home setting, the procedures of their use are less than desirable in a situation where many different tests must be conducted on a regular, frequent basis, for example at a drug testing laboratory.

It would be highly desirable to be able to test a single fluid specimen for a number of different substances using a compact, unitary device which requires no measuring or timing. Moreover, it would be advantageous if such a device was designed to require minimal handling, was sanitary to use and did not require separate caps or coverings to prevent contamination of the laboratory work table.

The present invention provides a sample fluid test card device containing single or multiple test strips for assaying a fluid specimen. The present device promotes hygienic laboratory conditions, is easy to use, and facilitates the assaying process in comparison to currently available assaying devices.

SUMMARY OF THE INVENTION

Accordingly, an analyte assaying device with a unique sample introduction system is provided. The device enables automatic specimen volume measurement, automatic controlled specimen metering, no wet contact of the device with the laboratory counter top, controlled flow venting for preventing test strip flooding and other advantages features which facilitate assaying of a fluid specimen.

Generally, the device comprises a casing and means, disposed in the casing, for assaying a fluid specimen, for example, but not limited to a biological fluid specimen, for example urine. The assaying means preferably comprises a testing assembly including at least one test strip element, disposed within the casing. In one embodiment of the invention, the test assembly comprises multiple lateral flow test strips for enabling several different assays to be performed on a single fluid specimen. Each test element includes a sample introduction region and a detection region where chemical interactions take place to reveal a presence or absence of an analyte of interest depending upon the assaying test being performed. The test assembly preferably further comprises a sample pad for receiving the fluid sample, and an absorbent end pad. The sample pad may overlap the sample introduction region of each of the test elements. The fluid specimen absorbed by the sample pad then permeates and is absorbed by the sample introduction region of the test element and migrates into the detection region by capillary action. The absorbent end pad, provides means for absorbing any excess fluid or moisture in the casing before, during and/or after the assaying procedure.

The casing preferably comprises a cover, a base, a pocket portion and an observation portion. The cover and base form a substantially hollow cavity within the casing in which the testing assembly is disposed. Multiple frets are defined by interior surfaces of the cover and/or base in order to secure alignment of the test elements.

The observation portion of the casing defines at least one window opening for enabling observation of portions of the test elements. For example, multiple window openings may be provided for enabling observation of test results displayed on one or more portions of each of the testing elements. Alternatively, the casing may be at least partially transparent in order to enable visual observation of the test elements. For example the casing may include no window openings and may be made of a clear plastic material.

Importantly, the pocket portion defines a pocket sized to contain a predetermined volume of the fluid sample to be tested. In the multiple test element embodiment of the invention, the pocket is sized and adapted to contain at least a volume of fluid that is sufficient to run all of the multiple test elements to completion after a quick (e.g. between about one second and five seconds) dip into the test fluid. Consideration is given to any amount of fluid that will naturally be retained by the sample pad after the assaying procedure has run to completion.

The device in accordance with the present invention further includes means for automatic controlled metering of the fluid specimen onto the sample pad. More specifically, the pocket portion of the casing further includes a feed element having at least one feed inlet defined therein for providing fluid transfer between the pocket and the testing assembly. The feed element projects from the interior surface of the casing cover and provides pressure against the sample pad. Advantageously, the structure of the feed element and feed inlets and their relationship with the sample pad, assure a metered, controlled release of the fluid sample, thus preventing saturation of the test assembly and flooding of the casing cavity. This feature of the present invention functions to control specimen metering regardless of whether the device is vertically positioned or horizontally positioned, the importance of which will become better appreciated upon further review of the present description.

The pocket portion is preferably sized and shaped to facilitate capture of the predetermined volume of fluid when the pocket portion of the device is momentarily submerged in a fluid specimen, for example a urine specimen contained in a collection cup. The base and cover are sealed at adjoining edges thereof to prevent fluid from entering the casing from anywhere other than through the feed inlets in the pocket portion.

Another advantageous feature of the present invention includes support means, defined for example by a depending portion of the base, for propping or elevating the pocket portion of the casing when the device is placed on a level surface, in a substantially horizontal position, for example a laboratory counter top. This feature of the device is designed to enhance cleanliness of a laboratory in which many assaying procedures may be regularly conducted. More specifically, the support means is designed to prevent any "wet" contact of the pocket portion of the device, particularly after the pocket portion has been dipped or submerged in the fluid specimen. Advantageously, this allows a laboratory technician to dip or submerge the device in the collection cup in order to obtain the appropriate volume of fluid to run the test, and thereafter immediately place the device aside directly on the counter top without causing any wet contact between the device and the counter top. Moreover, with the present invention there is no need for special racks, hooks, support trays or other holders for supporting the device while the chemical reactions are taking place.

As an alternative procedure of use, the device may initially be placed on the laboratory counter top, in the horizontal position, and fluid specimen transferred from a source into the casing pocket by means of a pipette for example. The technician would simply fill the pocket without the need for any precise measurement, as the pocket is sized to contain the proper amount of fluid sample. The fluid sample will be absorbed at the appropriate rate from the supply held in the pocket.

Another feature of the present invention is means for facilitating manual handling of the device. For example the casing may be configured with appropriate recesses and/or textured gripping surfaces appropriately positioned to facilitate the manual handling of the device when the device is dipped into or otherwise submerged in the specimen.

BRIEF DESCRIPTION OF THE DRAWINGS

The present invention and the objects and advantages of will be more clearly understood and appreciated with reference to the following detailed description when considered in light of the accompanying drawings of which:

FIG. 6b shows a cross sectional view of the device 10 including the alternative pocket portion shown in FIG. 6a.

DETAILED DESCRIPTION

Figure 1:
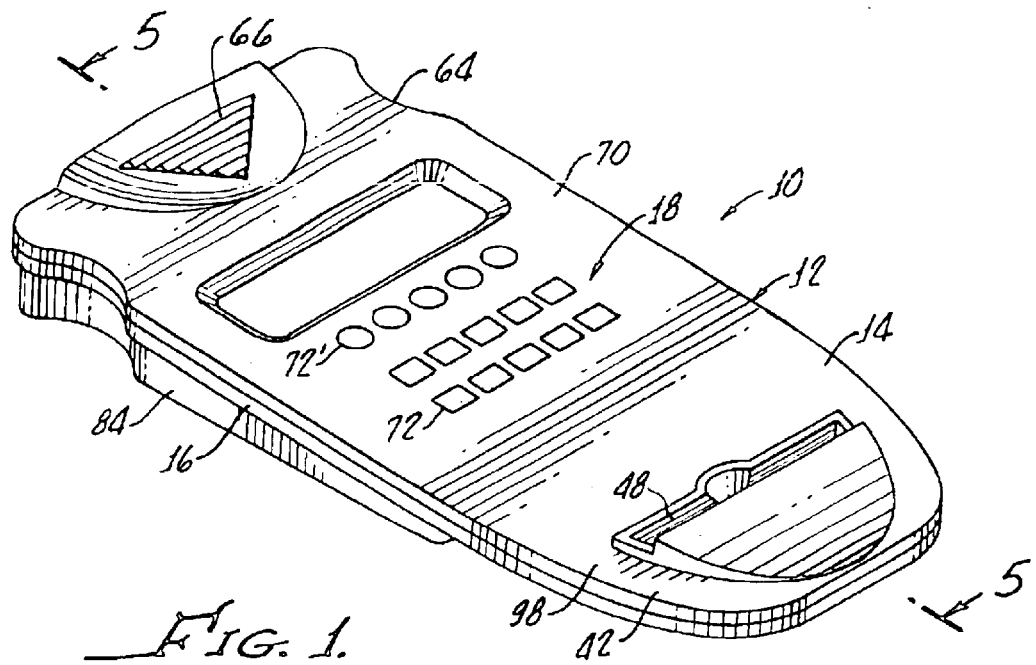
FIG. 1 shows a perspective view of an analytical test device in accordance with the invention, the device generally including a cover and a base.
Figure 2:
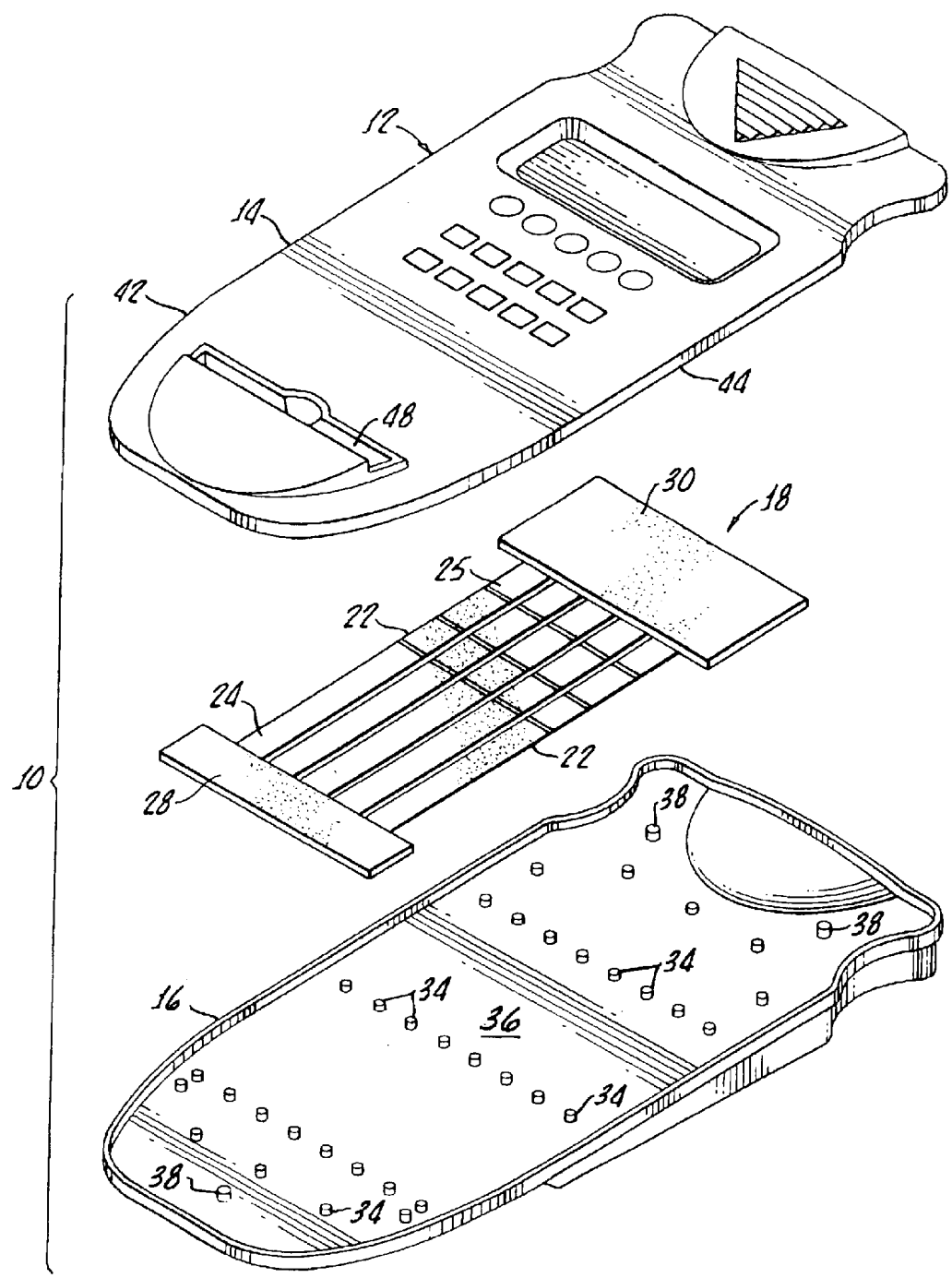
FIG. 2 shows an exploded view of the device shown in FIG. 1.
Figure 3:
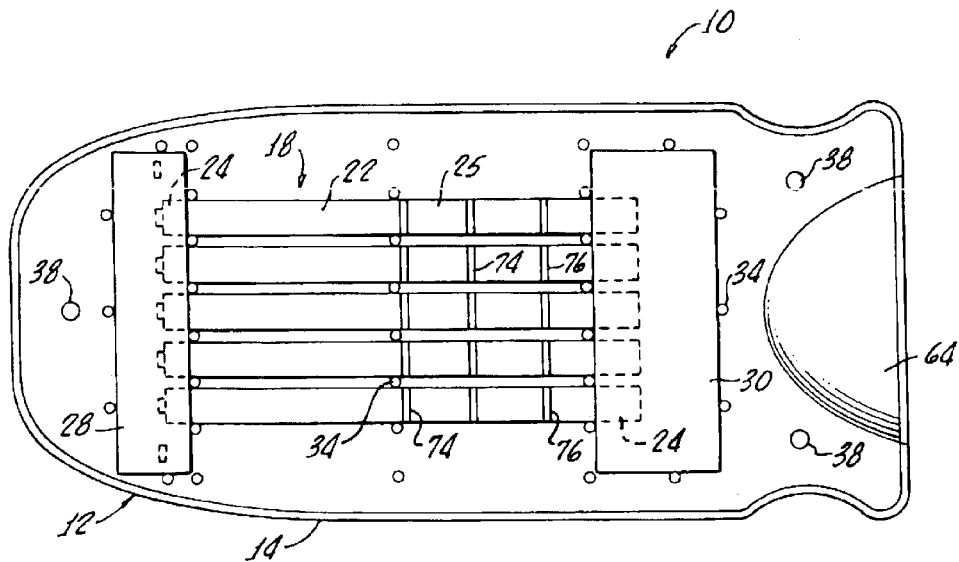
FIG. 3 shows a top plan view of the device shown in FIG. 1, with the cover removed therefrom.

Turning now to FIGS. 1, 2 and 3, an analytical test device 10 in accordance with the present invention is shown. The device 10 generally comprises a casing 12 including a cover 14, a base 16, and a testing assembly 18, disposed generally between the cover 14 and base 16, providing means for assaying a biological fluid specimen, for example but not limited to, urine.

The casing 12 may be made of any suitable material such, for example, plastic with the cover 14 and base 16 being molded separately and thereafter fastened together in a tight fit to ensure security against ingress of fluid through seams of the casing 12. Preferably, the cover 14 and base 16 are sonically welded together in order to provide a fluid tight seal therebetween.

Referring now specifically to FIGS. 2 and 3, the testing assembly 18 comprises at least one test element 22. In the shown embodiment, the testing assembly 18 comprises a plurality of test elements 22, for example five lateral flow test strips, as shown. For purposes of the present description, each test element 22 may be generally defined as including a sample introduction region 24, and a detection region 25. Each of the test elements 22 provides means for determining a presence, absence, or relative quantity of a substance of interest in a fluid sample absorbed into the sample introduction region 24 of the test element 22.

The testing assembly 18 preferably further comprises a sample receiving member 28, hereinafter referred to as a "sample pad 28", and a residual moisture absorbing member 30, hereinafter referred to as an "end pad 30". The sample pad 28 preferably overlaps or overlays the sample introduction region 24 of each of the test elements 22. The sample pad 28 may be comprised of any suitable porous material that will allow release of fluid into the test elements 22 when the sample pad 28 is in a moist state. When the fluid is deposited on the sample pad 28, as will be described hereinafter, the fluid will become absorbed by and permeate each and every test element 22 in contact with the pad 28. The fluid specimen will then migrate by capillary action through each and every test element 22 toward the residual moisture absorbing element 30.

Each test element 22 may be comprised of a porous carrier material, such as a rectangular, nitrocellulose test strip, having analyte specific reagent "zones" incorporated thereon in a conventional fashion. It is noted that manufacturing specifics of test elements 22 useful in the present invention are not described in great detail herein, as such details are well known and are not considered a part of the present invention. Any variety of materials, methods and manufacturing techniques can be used for producing the test elements 22 in order to achieve the desired purpose.

For example, the reagents can be applied to the carrier material in a variety of ways. Various printing techniques have previously been proposed for application of liquid reagents to carriers, for example, micro-syringes, pens using metered pumps, direct printing and ink-jet printing, and any other conventional technique may be used in the context of the present invention. To facilitate manufacture of a number of identical test elements, a sheet of porous carrier material may be treated with reagents and then the sheet cut into smaller portions (e.g. strips) each embodying the required reagent containing zones.

Figure 4:
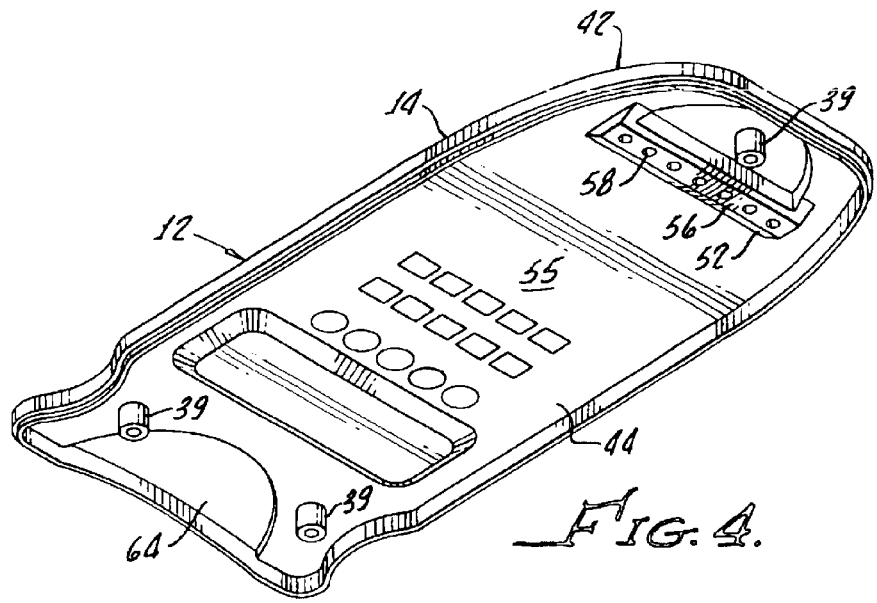
FIG. 4 shows a perspective view of an interior surface of the cover.

The base 16 of the casing 12 preferably includes positioning means for aligning and/or securing the test assembly in the casing. For example, as shown in FIG. 2, multiple frets 34 project from and are defined by an interior surface 36 of the base 16. The shown layout of frets 34 function to maintain the spaced apart relationship of the test elements 22, and secure the desired positional arrangement of the test elements 22, the sample pad 28 and the end pad 30. Alternatively or additionally, frets or other positioning means may be provided on the casing cover 14. Turning as well now to FIG. 4, fastening elements 38, 39 may be provided for engaging the cover 14 and the base 16.

Referring now particularly to FIGS. 1 and 4, the casing 12 includes a chamber 42 and an observation portion 44. More specifically, the chamber 42 defines a pocket 48 sized and adapted to contain a predetermined volume of a fluid sample. The pocket 48 is sized for containing a predetermined volume of fluid specimen necessary to run all of the test elements 22 to completion following quick momentary submersion into the test fluid. As a specific example, device 10 is adapted to accommodate five test elements 22 and each test element 22 requires about 50 microliters (which is about one drop) of fluid (e.g. urine) for completion. Consideration is of course given to the small volume of fluid that will naturally be retained by the sample pad 28. The pocket 48 in this example is sized to contain about 0.3 mL (i.e. 300 microliters) of urine.

Figure 5:
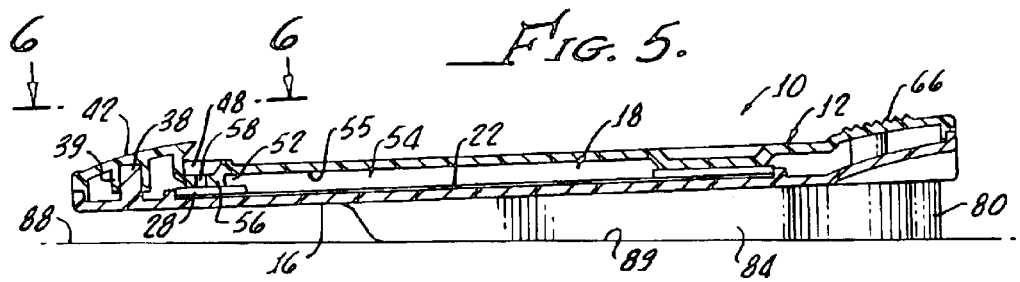
FIG. 5 shows a cross sectional view of the device, taken across line 5—5 of FIG. 1.
Figure 6:
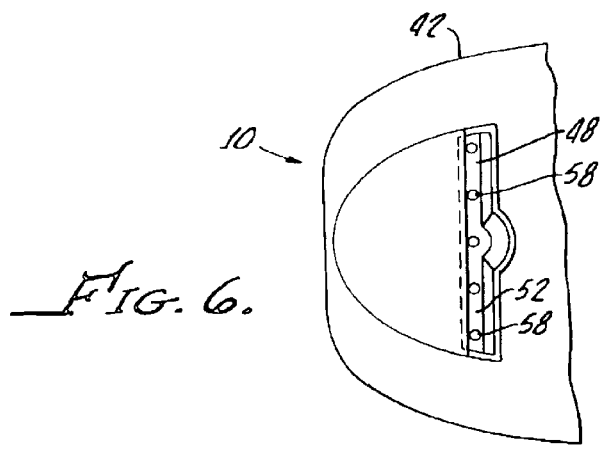
FIG. 6 shows a partially cut away view of a pocket portion of the device shown in FIG. 1 taken along 6—6 of FIG. 5.

Importantly, the chamber 42 further defines a feed element 52, shown in FIGS. 4 and 5. As shown in Figure 5, the cover 14 and base 16 define a generally hollow cavity 54 in which the testing assembly 18 is disposed. The feed element 52 is defined by an interior surface 55 of the casing cover 14. Referring now briefly to FIG. 4, the feed element 52 includes a generally planar surface 56. Turning as well to FIG. 6, the generally planar surface 56 is in contact with and importantly, provides pressure against the sample pad 28. Advantageously, the structure of the feed element 52 and the pressure thereof against the sample pad 28 feature provides means for automatic controlled specimen metering of the fluid specimen from the pocket 48 and onto the sample pad 28, after the device 10 is manually dipped (preferably for a maximum duration of between about one second and about five seconds) into the test fluid.

Figure 7:
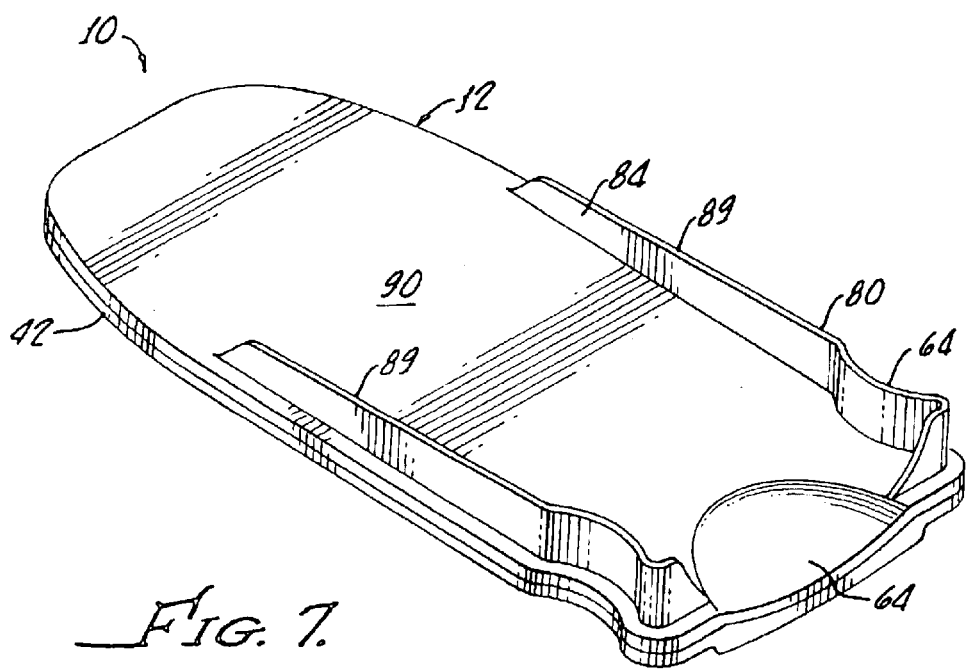
FIG. 7 shows a perspective view of a bottom of the device shown in FIG. 1.

The feed element 52 includes at least one feed inlet 58 defined through the generally planar surface 56 of the feed element 52. A plurality of feed inlets 58 may be provided as shown in FIGS. 4 and 6. Alternatively, as shown in FIG. 7, a single elongated feed inlet 58, defined along the length of the feed element 52 may be provided. Importantly, the feed element 52 is designed to provide sufficient pressure between the generally planar surface 56 and the sample pad 28 in order to control a rate of fluid release.

Preferably, each one of the plurality of feed inlets 58 is generally aligned with one of the test elements 22. The multiple inlets 58 are preferably equidistantly spaced apart from one another along the feed element 52. In one embodiment of the invention, at least five feed inlets 58 and up to seven feed inlets 58 are provided, wherein each of the feed inlets 58 has a diameter of about 0.042 inches.

The small size each of the plurality of feed inlets 58, and the pressure provided by the feed element 52 against the sample pad 28 assures a controlled release of the fluid sample contained in the pocket 48 through the inlets 58. Advantageously, this provides for an automatic, controlled rate of absorption of fluid by the sample pad 28 and prevents the device 10 from flooding by fluid entering the casing cavity 54 too rapidly through the inlets 58.

As the sample pad 28 absorbs the fluid through the small inlets 58, the fluid will permeate and become absorbed by each test element 22 at a suitable rate, and in substantially equal proportions, for the chemical reactions to take place. Likewise, for the single feed inlet 58a shown in FIGS. 6a and 6b, the length and width of the feed slot 58a determines the rate of absorption of fluid by the sample pad 28.

Figure 6B:
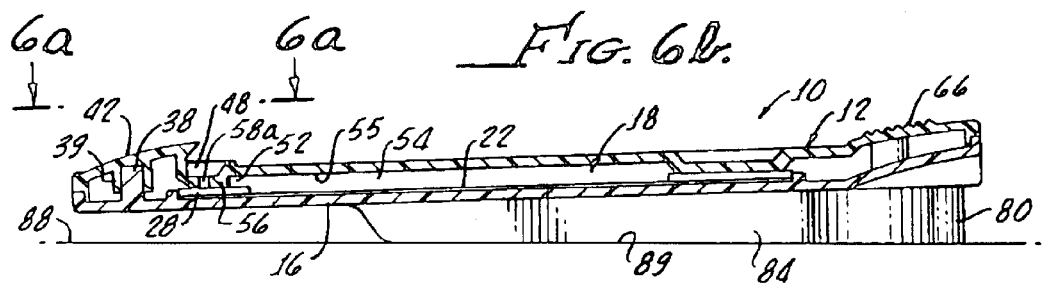
Figure 6A:
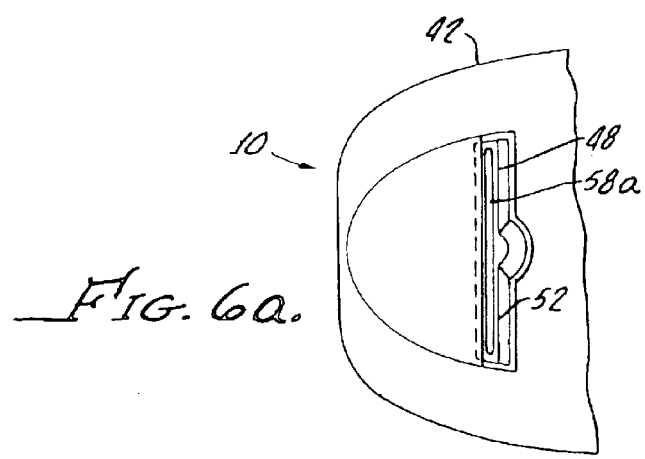
FIG. 6a shows a partially cut away view of an alternative pocket portion of the device shown in FIG. 1.

Referring now to FIGS. 6a, an alternative feed inlet 58a in accordance with the invention, comprises, for example, a single slot 58a defined along feed element 52a. The feed inlet slot 58a is, for example, about one inch long and about 0.050 inches in width. More generally, the feed inlet 58a is preferably sufficiently long to extend across each of the test elements 22 disposed in the casing 12.

Like the feed element 52 described hereinabove, and shown in FIG. 6, the alternative feed element 52a includes a flat portion 56a (see FIG. 6b). The flat portion 56a is in contact with and pressed against the sample pad 28. The pressure of the feed element 52a against the sample pad 28 and the size of the feed inlet slot 58a controls the rate of fluid release from the pocket 58 and the rate of fluid absorption by the sample pad 28.

As described above, the feed inlet 58a or plurality of feed inlets 58 are sized sufficiently small to provide an appropriate rate of fluid transfer from the pocket 48 to the testing assembly 18, more specifically to the sample pad 28.

The appropriate volume of fluid sample for running the test may be deposited in the pocket 48 by simply dipping the chamber 42 of the device 10 into a fluid collection cup (not shown) containing a urine specimen. No precise timing is necessary. A brief one second to about five second dip assures that the appropriate volume of test fluid will be deposited in the pocket 48.

Importantly, as mentioned hereinabove, the device 10 is dipped into the urine specimen for only brief moment. If the device 10 is held too long in the fluid specimen, the device may become flooded and the test fail. It has been found that a dip lasting between about one second and about five seconds is typically sufficient to fill the pocket without flooding the device.

Alternatively, a small amount of urine sample may be deposited into the pocket 48, for example, by using a small pipette (not shown) or other means to transfer fluid specimen into the pocket 48. The laboratory's selected operating procedure will typically determine if the device 10 is dipped into the urine specimen or if a pipette is used to transfer the urine into the pocket 48.

It has been found that when the pipette method is used to transfer fluid into the pocket 48, the device 10 operates more effectively when the feed inlet comprises the slot shaped feed inlet 58a shown in FIGS. 6a and 6b. Both designs worked well when the dipping method was used. However, when using the pipetting method and the multiple feed inlets 58, occasionally one or more of the inlets 58 would not fill consistently. Although not wishing to be bound by any particular theory of operation, it is believed that when using the pipetting method, there is insufficient hydrostatic pressure to displace air and fill all of the inlets 58 consistently with the small volume of test fluid, namely urine, in the pocket 48. When inlet size is increased, the test device 10 would occasionally flood. It was found that the feed inlet slot 58a, along with adequate pressure against the sample pad 28, provided beneficial results when the urine sample was transferred to the pocket 48 by pipette technique. It was also found that acceptable test results were achieved by quickly submersing the pocket portion 42 of the device 10 (with either multiple feed inlets 58 or single slot feed inlet 58a), into a container holding the test fluid, and removing the device 10 within the first five seconds.

In addition, the device 10 may include grip means, for example contours 64 and textured finger grip 66 for facilitating manual handling of the device 10. The molded contours 64 and textured grip 66 are positioned on the casing 12 in a manner which will assist a user of the device 10 in effectively dipping, or partially submerging, the device 10 into a fluid collection container (not shown) to obtain an appropriate amount of fluid specimen in the pocket 48.

Turning back now to FIG. 1, the casing 12 further includes an observation portion 70, defining for example at least one window opening 72, for enabling observation of test results. Alternatively, the casing cover 14 may be comprised of a clear plastic material or the like. In the shown embodiment, the plurality of test elements 22 enable five different tests to be performed on a single fluid specimen absorbed by sample pad (not shown in FIG. 1). In this embodiment 10, multiple window openings 72 are provided, each window 72 revealing a particular reagent zone 74 (see FIG. 3) of the test elements 22. Additional windows, for example round windows 72' may be provided, each for revealing a control zone 76 (see FIG. 3) of each test strip 22, to provide a visual indication of test validity and to gauge assay completion.

Attention is now directed specifically to FIG. 5. The present invention 10 preferably further comprises support means 80, for example a rail 84 or other structure depending from the casing 12, for preventing "wet" contact of the device 10 with a table or counter top 88 while assaying is taking place. Turning now as well to FIG. 7, which shows an underside surface 90 of the base 16, the rail 84 is shown as being disposed along a portion of a perimeter of the base 16. The rail 84, or more specifically, a surface contact edge 89 of the rail 84, does not extend as far as the pocket portion 42 of the casing 12. The rail 84 is structured to elevate the pocket portion 42 above the surface 88 upon which the device is placed, when the device 10 is disposed in a substantially horizontal position.

Advantageously, the support means 80 allows a laboratory technician to briefly dip or submerge the device 10 in a collection cup (for between about one and about five seconds) in order to capture, in the pocket 48, the appropriate volume of fluid specimen required without a precise timing step. Thereafter, the technician can immediately place the device 10 on the laboratory counter top 88 without causing any wet contact therewith. The technician can attend to other matters while the assay is taking place.

The present device 10 is designed to be very easy to use and requires no precise measurements of fluid volume or timing. Moreover, a complete assaying test, even a test for multiple analytes, can be performed with a single manual step when using the device 10 of the present invention.

More particularly, once a specimen has been collected in a collection cup (not shown), for example after a test subject has filled a collection cup with urine, the technician or analyst can perform the entire assaying procedure by grasping the device 10 by contours 64 and finger grip 66 and dipping the device 10 into a fluid specimen, at least up to a "fill-line" 98 (see FIG. 1), but not as far as the observation windows 72. After briefly dipping the device 10 in the specimen, the device 10 may then be touched to an edge of the collection container to remove any droplets of urine adhering to the casing 12, particularly on the dipped portion (i.e. chamber 42) of the casing 12. The device 10 having the pocket 48 filled with the fluid specimen is then placed on the table or counter top 88 in the horizontal position, such as shown in FIG. 5.

Advantageously, the damp or wet portion (i.e. chamber 42) of the device 10 is supported above and out of contact with the table or counter top 88 by means of the rail 84 depending from the base 16. This feature is designed to enhance laboratory efficiency and cleanliness, particularly in a laboratory where frequent and numerous assaying tests must be performed on a limited work space and within a short time period. For example, a potential time savings may be realized by minimizing work surface contamination since the fluid specimen is kept completely out of contact with the work surface even though the device is placed directly on the work surface as shown. It can be appreciated by those of skill in the art that the assaying device 10 in accordance with the invention is designed to contributes to a cleaner, more sanitary work area than conventional dip-and-read devices which require either the device be manually held during the testing procedure, hooked on the collection container, or placed in a wet condition on a work surface.

Although there has been hereinabove described a multiple analyte assaying device with a multiple sample introduction system, in accordance with the present invention, for purposes of illustrating the manner in which the invention may be used to advantage, it will be appreciated that the invention is not limited thereto. Accordingly, any and all modifications, variations, or equivalent arrangements which may occur to those skilled in the art should be considered to be within the scope of the present invention as defined in the appended claims.

What is claimed is:

1. An analytical test device comprising:

a casing;

a sample meter for controlling a release rate of fluid sample, said sample meter comprising a sample pad and a feed element having a generally planar surface pressed against said sample pad and at least one feed inlet through the planar surface for providing fluid communication, said fluid element being disposed with sufficient pressure between the generally planar surface and the sample pad in order to control a rate of fluid sample release;

a chamber defining a pocket extending outwardly from said casing and sized and shaped to capture and contain a preselected volume of the fluid sample, said volume providing sufficient hydrostatic pressure to displace air and fill the inlets with fluid sample;

a testing assembly, disposed in the casing, for assaying the released fluid sample from the pocket; and a rail for supporting said casing on a generally horizontal surface with the pocket disposed in a spaced apart relationship with said generally horizontal surface.

2. The test device according to claim 1 wherein the at least one feed inlet comprises a plurality of spaced apart feed inlets in said generally planar surface in order to provide controlled release of fluid in said pocket via hydrostatic pressure to the feed element.

3. The teat device according to claim 1 wherein the at least one feed inlet comprises a slot in said generally planar surface in order to provide controlled release of fluid in said pocket via hydrostatic pressure to the feed element.

4. The test device according to claim 1 wherein said testing assembly comprises a plurality of spaced apart test strips each communicating with said sample meter.

5. The test device according to claim 1 further comprising a grip positioned on said casing for facilitating dipping the device into a fluid container in order to fill said pocket with fluid sample.

* * * * *

UNITED STATES PATENT AND TRADEMARK OFFICE
CERTIFICATE OF CORRECTION

PATENT NO. : 6,833,111 B2  
DATED : December 21, 2004  
INVENTOR(S) : John L. Robertson et al.

It is certified that error appears in the above-identified patent and that said Letters Patent is hereby corrected as shown below:

<u>Title page,</u>  
Item [75], Inventors, please change "John L. Robertson, Fisher, IN (US)" to -- John L. Robertson, Fishers, IN (US) --.

Signed and Sealed this

Twelfth Day of April, 2005

JON W. DUDAS  
*Director of the United States Patent and Trademark Office*

UNITED STATES PATENT AND TRADEMARK OFFICE
CERTIFICATE OF CORRECTION

PATENT NO.     : 6,833,111 B2                                    Page 1 of 1
DATED          : December 21, 2004
INVENTOR(S)    : John L. Robertson et al.

It is certified that error appears in the above-identified patent and that said Letters Patent is hereby corrected as shown below:

<u>Title page,</u>
Item [73], Assignee, please change "Roche Diagnostics Corp.," to -- Roche Diagnostics Operations, Inc. --.

Signed and Sealed this

Twenty-sixth Day of July, 2005

JON W. DUDAS
*Director of the United States Patent and Trademark Office*